(12) United States Patent
Libbus et al.

(10) Patent No.: US 7,647,101 B2
(45) Date of Patent: Jan. 12, 2010

(54) PHYSICAL CONDITIONING SYSTEM, DEVICE AND METHOD

(75) Inventors: Imad Libbus, St. Paul, MN (US); Julio C. Spinelli, Shoreview, MN (US); Joseph M. Pastore, Woodbury, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 372 days.

(21) Appl. No.: 11/423,249

(22) Filed: Jun. 9, 2006

(65) Prior Publication Data

US 2007/0288070 A1 Dec. 13, 2007

(51) Int. Cl.
*A61N 1/00* (2006.01)
(52) U.S. Cl. .......................................................... 607/2
(58) Field of Classification Search .................. 607/46, 607/2–28
See application file for complete search history.

(56) References Cited

U.S. PATENT DOCUMENTS

| | | | |
|---|---|---|---|
| 5,700,282 A | 12/1997 | Zabara | |
| 6,400,982 B2 * | 6/2002 | Sweeney et al. | 600/515 |
| 6,937,896 B1 * | 8/2005 | Kroll | 607/9 |
| 7,123,961 B1 | 10/2006 | Kroll et al. | |
| 7,305,266 B1 * | 12/2007 | Kroll | 607/28 |
| 7,403,821 B2 * | 7/2008 | Haugland et al. | 607/49 |
| 2002/0107553 A1 * | 8/2002 | Hill et al. | 607/18 |
| 2002/0116030 A1 | 8/2002 | Rezai | |
| 2003/0181951 A1 | 9/2003 | Cates | |
| 2004/0059392 A1 * | 3/2004 | Parramon et al. | 607/36 |
| 2004/0186525 A1 | 9/2004 | Burnes et al. | |
| 2006/0095080 A1 | 5/2006 | Libbus et al. | |
| 2006/0095081 A1 * | 5/2006 | Zhou et al. | 607/2 |
| 2006/0106429 A1 | 5/2006 | Libbus et al. | |
| 2006/0116721 A1 * | 6/2006 | Yun et al. | 607/2 |
| 2006/0116736 A1 * | 6/2006 | DiLorenzo | 607/40 |
| 2006/0116737 A1 | 6/2006 | Libbus | |
| 2006/0253161 A1 | 11/2006 | Libbus et al. | |
| 2006/0293714 A1 * | 12/2006 | Salo et al. | 607/9 |
| 2007/0173899 A1 * | 7/2007 | Levin et al. | 607/40 |

FOREIGN PATENT DOCUMENTS

WO   WO 2007/146490 A2   12/2007

OTHER PUBLICATIONS

"PCT Application No. PCT/US2007/066918, International Search Report mailed Mar. 10, 2008", 6 pgs.
"PCT Application No. PCT/US2007/066918, Written Opinion mailed Mar. 10, 2008", 10 pgs.
Adamopoulos, S., "Effects of Pulsed β-Stimulant Therapy on β-Adrenoceptors and Chronotropic Responsiveness in Chronic Heart Failure.", *Lancet*, 345(8946), (1995), 344-349.

(Continued)

*Primary Examiner*—Scott M Getzow
(74) *Attorney, Agent, or Firm*—Schwegman, Lundberg & Woessner, P.A.

(57) ABSTRACT

Various system embodiments comprise a neural stimulator and a controller. The neural stimulator is adapted to generate a stimulation signal adapted to elicit sympathetic activity at a neural target. The controller is adapted to control the neural stimulator to provide a physical conditioning therapy. The controller is adapted to control the neural stimulator to intermittently elicit sympathetic activity at the neural target. Other aspects and embodiments are provided herein.

38 Claims, 11 Drawing Sheets

OTHER PUBLICATIONS

Coats, A. J., "Controlled Trial of Physical Training in Chronic Heart Failure. Exercise Performance, Hemodynamics, Ventilation, and Autonomic Function", *Circulation*, 85(6), (1992), 2119-2131.

Hautala, A., "Effect of Physical Exercise on Autonomic Regulation of Heart Rate", *Effect of Physical Exercise on Autonomic Regulation of Heart Rate, Oulu University Press, Department of Internal Medicine*, (2004), 1-76.

Leier, C. V., "Drug-induced Conditioning in Congestive Heart Failure", *Circulation*, 65(7) 1982, 1382-1387.

Liang, C., "Conditioning Effects of Chronic Infusions of Dobutamine. Comparison with exercise training.", *Journal of Clinical Investigation*, 64(2), (1979), 613-619.

Liang, C. S., "Sustained Improvement of Cardiac Function in Patients with Congestive Heart Failure After Short-Term Infusion of Dobutamine", *Circulation*, 69(1), (1984), 113-119.

Tohmeh, J. F., "Biphasic Adrenergic Modulation of β-Adrenergic Receptors in Man. Agonist-Induced Early Increment and Late Decrement in β-Adrenergic Receptor Number", *J Clin Invest.*, 65(4), (1980), 836-840.

\* cited by examiner

US 7,647,101 B2

PHYSICAL CONDITIONING SYSTEM, DEVICE AND METHOD

FIELD OF THE INVENTION

This application relates generally to medical devices and, more particularly, to systems, devices and methods for providing physical conditioning.

BACKGROUND

Dobutamine is a synthetic derivative of dopamine characterized by prominent inotropic but weak chronotropic and arrhythmogenic properties. Dopamine is a precursor of norepinephrine and epinephrine; and dopamine, norepinephrine and epinephrine are catecholamines associated with a sympathetic response to stress. Dobutamine provides a pharmaceutical means for providing sympathomimetic stimulation (stimulation that mimics the actions of the sympathetic system).

Animal studies have shown that intermittent sympathomimetic stimulation with dobutamine can produce beneficial changes analogous to the effects of physical training. In a controlled study of moderate to severe heart failure patients, short-term sympathetic stimulation with dobutamine (30 minutes/day, 4 days/week, for 3 weeks), was associated with a significant improvement in symptoms, autonomic balance, and chronotropic detrimental down-regulation responsiveness. Benefits of short-term sympathetic stimulation with dobutamine included increased exercise tolerance, improved heart rate variability, lowered peripheral vascular resistance, and reduced plasma noradrenaline. The short stimulation periods, in contrast to studies with long-term dopamine infusion, were not associated with detrimental down-regulation of β-receptors.

SUMMARY

Various aspects of the present subject matter relate to a system. Various system embodiments comprise a neural stimulator and a controller. The neural stimulator is adapted to generate a stimulation signal adapted to elicit sympathetic activity at a neural target. The controller is adapted to control the neural stimulator to provide a physical conditioning therapy. The controller is adapted to control the neural stimulator to intermittently elicit sympathetic activity at the neural target.

Various aspects of the present subject matter relate to a method. According to various embodiments of the method, a physical conditioning therapy is provided. Providing a physical conditioning therapy includes intermittently stimulating a neural target to elicit a sympathetic response.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
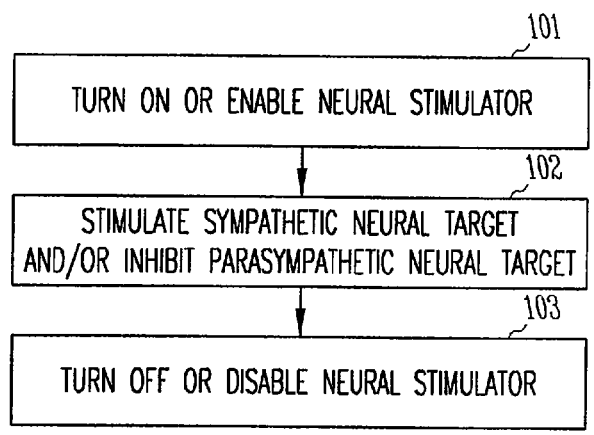
FIG. 1 illustrates a method for providing physical conditioning, according to various embodiments of the present subject matter.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some medical device embodiments stimulate a sympathetic neural target to provide the physical conditioning therapy, some medical device embodiments inhibit a parasympathetic neural target to provide physical conditioning therapy, and some medical device embodiments provide both sympathetic stimulation and parasympathetic inhibition for a physical conditioning therapy. Various embodiments provide an external neural stimulator to transcutaneously provide the neural stimulation and/or inhibition, and various embodiments provide an internal neural stimulator to provide the neural stimulation and/or inhibition. Examples of neural targets to provide sympathetic stimulation include the sympathetic column in the spinal cord, cardiac post-ganglionic sympathetic neurons, and the peroneal nerve behind the knee. Examples of a neural targets to provide parasympathetic inhibition include vagus, aortic and carotid nerves and branches thereof, cardiac fat pads, and baroreceptors such as baroreceptors in the aortic arch or carotid sinus. These neural target examples are not intended to be an exhaustive list of all possible neural targets. According to various embodiments, efferent and/or afferent neural pathways can serve as targets.

Various embodiments provide an electrical vector between two electrodes or among multiple electrodes to provide the stimulation or inhibition of nerve traffic. Other means for stimulating or inhibiting nerve traffic can be used. For example, ultrasound stimulation, light stimulation and magnetic stimulation of nerves have been proposed.

Various embodiments provide a programmable pulse generator to deliver intermittent short periods of sympathetic stimulation and/or parasympathetic inhibition to mimic the effects of physical training. For example, the physical conditioning provided by the sympathetic stimulation and/or parasympathetic inhibition can occur on a daily basis for about 30 minutes/day. The therapy is of a relatively short duration. Embodiments provide therapy on the order of 2 hours or less. The physical conditioning therapy provided by the neural stimulation device can be programmed to correlate to a suitable exercise regimen for the patient. For example, the above-identified 30 minutes/day of neural stimulation can correspond to 30 minutes/day of walking. In another embodiment, by way of example, the present subject matter can provide physical conditioning therapy that corresponds to an every other day exercise regimen. In an embodiment, a patient or health-care provider controls the times when the therapy is initiated and terminated. Safety measures can be provided to prevent therapies of excessive duration. Closed-loop feedback of a physiological variable can be used to acutely titrate the therapy to achieve a desired response (e.g. to achieve and maintain a target heart rate zone during exercise or achieve a desired heart rate profile in which the heart rate increases and decreases) or abruptly terminate the therapy when the physiological response is adverse or otherwise indicates that the patient is not tolerating the therapy. The feedback can be used to adjust the intensity of the sympathetic stimulation/parasympathetic inhibition by appropriately adjusting the frequency and duration of the periods of sympathetic stimulation, and/or adjusting stimulation parameters.

Embodiments of the present subject matter provide heart failure therapy using physical conditioning. However, physical conditioning via sympathetic stimulation/parasympathetic inhibition is applied to any patient who may benefit from physical conditioning, but is unable to tolerate physical exercise. The present subject matter can be incorporated as a stand-alone neural stimulator, or integrated into an existing CRM device for comprehensive heart failure therapy, for example.

The remainder of this disclosure further elaborates on aspects and embodiments of the present subject matter. An overview of some physiology is provided to assist with understanding physical conditioning therapy and other therapies discussed thereafter. Some embodiments combine or integrate physical conditioning therapy with other therapies. Also discussed below are device embodiments and system embodiments.

Physiology

In addition to being used to provide physical conditioning therapy, the nervous system can be used to provide therapy for heart failure, hypertension, and cardiac remodeling. Therefore, this brief overview includes a brief discussion of the nervous system, heart failure, hypertension and cardiac remodeling.

Nervous System

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with the genesis of various arrhythmias, including ventricular tachycardia and atrial fibrillation.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed, including anodal block of nerve traffic. According to various embodiments of the present subject matter, sympathetic neural targets include, but are not limited to, a peroneal nerve, a sympathetic column in a spinal cord, and cardiac post-ganglionic sympathetic neurons. The physical conditioning therapy can be accomplished by stimulating neural activity at a sympathetic neural target. According to various embodiments of the present subject matter, parasympathetic neural targets include, but are not limited to, a vagus nerve, a baroreceptor, and a cardiac fat pad. The physical conditioning therapy can be accomplished by inhibiting neural activity at a parasympathetic neural target.

Heart Failure

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

Hypertension

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac Remodeling

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapies

The present subject matter relates to systems, devices and methods for providing physical conditioning using sympathetic stimulation and/or parasympathetic inhibition. Various embodiments provide a stand-alone device, either externally or internally, to provide physical conditioning. Various embodiments provide systems or devices that integrate physical conditioning therapy with one or more other therapies, such as bradycardia pacing, anti-tachycardia therapy, remodeling therapy, and the like.

Physical Conditioning Therapy

It is generally accepted that physical activity and fitness improve health and reduce mortality. Studies have indicated that aerobic training improves cardiac autonomic regulation, reduces heart rate and is associated with increased cardiac vagal outflow. A baseline measurement of higher parasympathetic activity is associated with improved aerobic fitness. Exercise training intermittently stresses the system and increases the sympathetic activity during the stress. However, when an exercise session ends and the stress is removed, the body rebounds in a manner that increases baseline parasympathetic activity and reduces baseline sympathetic activity.

Physical training stimulates the $\beta_1$-receptors of cardiac myocytes, which is a result of sympathetic stimulation. Short periods of exercise (e.g. less than 1-2 hours) result in an increase of $\beta_1$-receptor activity. On the other hand, periods of exercise longer than 2 hours can cause a reduction in $\beta_1$-receptor activity. Physical conditioning can be considered to be a repetitive, high-level exercise that occurs intermittently over time. The present subject matter mimics the effects of physical conditioning with sympathetic nerve stimulation and/or parasympathetic nerve inhibition.

FIG. 1 illustrates a method for providing physical conditioning, according to various embodiments of the present subject matter. A neural stimulator (understood to include devices that apply electrical stimulation that stimulates nerve traffic and/or inhibits nerve traffic) is turned on or otherwise enabled at 101. At 102, the device stimulates a sympathetic neural target, inhibits a parasympathetic neural target, or both stimulates a sympathetic neural target and inhibits a parasympathetic neural target. At 103, the device is turned off or otherwise disables the neural stimulator. In various external device embodiments, for example, the device includes a switch capable of being actuated by the patient or other person (e.g. physician) to turn the external device on and off. In various internal device embodiments, for example, the device is turned on and off through a wireless link. Examples of such wireless links include a magnetic field, and communications through induction, RF or ultrasound. Various embodiments provide user-initiated physical conditioning therapy (e.g. 101 in FIG. 1), where a user "turns on" the therapy, which runs for a preprogrammed time. Various embodiments provide user-terminated physical conditioning therapy (e.g. 103 in FIG. 1), where a programmed therapy is prematurely terminated by the user, regardless of whether the user initiated the physical conditioning therapy. Various embodiments provide user-titrated physical conditioning therapy, where the intensity and/or duration of the physical conditioning therapy can be increased or decreased by the user. The user can be a patient, a physician or other person. These user-initiated, user-terminated, and user-titrated embodiments can be internal or external devices. Various embodiments provide the ability for a user to perform all three functions (initiate, terminate and titrate), or any combination of two or more of these functions. An internal device embodiment uses an internal timer to turn the device on (e.g. 101 in FIG. 1) and off (e.g. 103 in FIG. 1). A pre-programmed schedule can control the on-time and off-time of the therapy. Other events can be used to either enable or disable the programmed on-time and off-time. For example, the programmed therapy can be enabled if the heart rate is within a predetermined zone, if the systolic blood pressure is within a predetermined zone, and/or the respiration rate is within a predetermined zone. A programmed therapy can be disabled or terminated if the heart rate is over a predetermined threshold, the systolic blood pressure is over a predetermined threshold, and/or the respiration rate is over a predetermined threshold.

Figure 2:
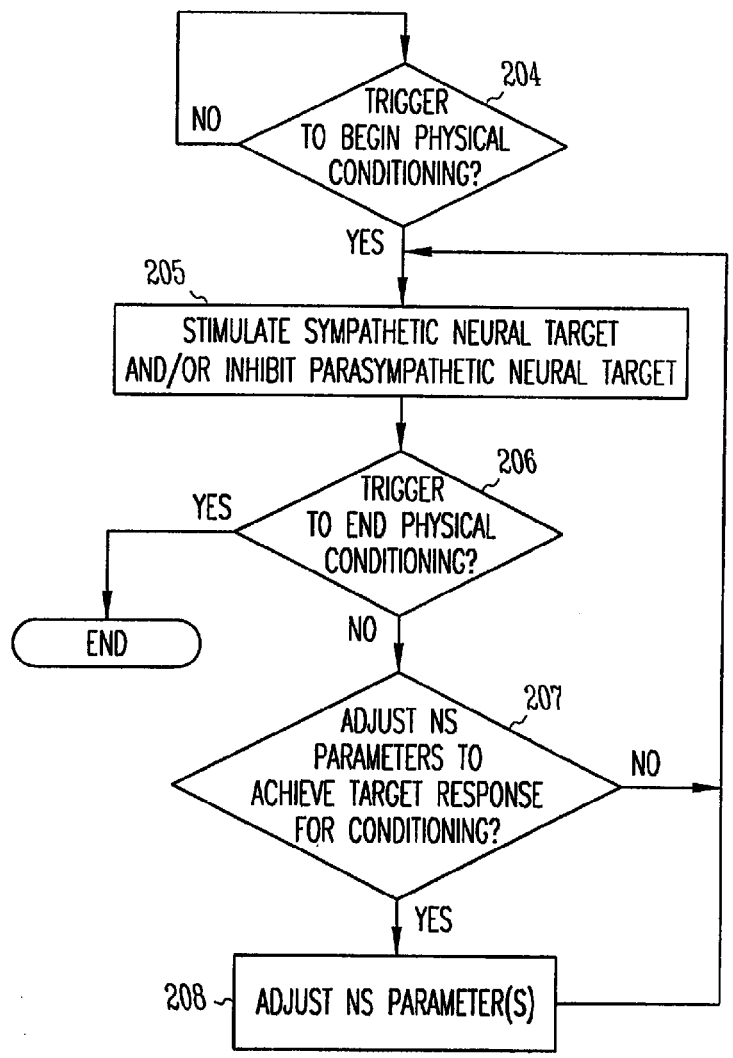
FIG. 2 illustrates a method for providing physical conditioning, according to various embodiments of the present subject matter.

FIG. 2 illustrates a method for providing physical conditioning, according to various embodiments of the present subject matter. At 204, it is determined whether a trigger has been received to begin physical conditioning. When the trigger is detected, a sympathetic neural target is stimulated and/or a parasympathetic neural target is inhibited at 205. At 206, it is determined whether a trigger to end the physical conditioning has been received. Various implantable device embodiments are triggered (e.g. 204 and 206) by an external signal controlled by a physician or patient. A device embodiment uses a timer to turn the device on (e.g. 204 in FIG. 2) and off (e.g. 206 in FIG. 2). A pre-programmed schedule can control the on-time and off-time of the therapy. Other events can be used to either enable or disable the programmed on-time and off-time. Various sensor feedback can be used to enable and/or disable the therapy. For example, the programmed therapy can be enabled if the heart rate is within a predetermined zone, if the systolic blood pressure is within a predetermined zone, and/or the respiration rate is within a predetermined zone. A programmed therapy can be disabled or terminated if the heart rate is over a predetermined threshold, the systolic blood pressure is over a predetermined threshold, and/or the respiration rate is over a predetermined threshold. If the trigger to end the therapy has not been received, it is determined at 207 whether to adjust the neural stimulation parameters to achieve a target response for the conditioning therapy. Adjustable neural stimulation parameters include, but are not limited to, a stimulation duration as well as an amplitude, frequency, pulse width, morphology, and burst frequency of the neural stimulation signal. These parameters can be appropriately increased or decreased to obtain a desired change in the intensity of the neural stimulation/inhibition. Examples of target responses include a target heart rate range or target blood pressure range or respiratory rate for a period of time. If it is determined at 207 to adjust the parameters, the process proceeds to 208 to adjust the parameter(s) and returns to 205; and if it is determined that the parameters will not be adjusted, the process returns from 207 to 205. Various embodiments provide target range(s) as programmable parameters, and various embodiments automatically adjust the intensity of the neural stimulation/inhibition to maintain a sensed physiological parameter (e.g. heart rate) within the target range. Various embodiments provide means for manually adjusting the intensity based on a sensed physiological parameter.

The physical conditioning therapy provided by the present subject matter can be applied as therapy for heart failure. The present subject matter stimulates a sympathetic target, inhibits a parasympathetic target, or both stimulates a sympathetic target and inhibits a parasympathetic target. The neural stimulation can be provided using electrical, acoustic, ultrasound, light, and magnetic therapies.

Examples of other physical conditioning therapies include therapies for patients who are unable to exercise. For example, physical conditioning using sympathetic stimulation/parasympathetic inhibition for a bed-bound, post-surgical patient in a hospital may enable the patient to maintain strength and endurance until such time that the patient is able to exercise again. By way of another example, a morbidly obese patient may be unable to exercise, but may still benefit from the physical conditioning therapy. Furthermore, patients with injuries such as joint injuries that prevent them from performing their normal physical activities may benefit from the physical conditioning therapy.

The physical conditioning therapy using sympathetic stimulation and/or parasympathetic inhibition can be combined with other therapies. Examples of such therapies include, but are not limited to, CRM functions such as bradycardia pacing and anti-tachycardia therapies, and cardiac resynchronization therapy, and further include neural stimulation therapy such as hypertension therapy, and remodeling therapy. These therapies are briefly discussed below.

Bradycardia Pacing/CRT Pacing

A pacemaker is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

Anti-Tachycardia Therapy

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modem ICDs typically have ATP capability, and deliver ATP therapy or a shock pulse when a tachyarrhythmia is detected.

Therapy for Cardiac Remodeling

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Neural Stimulation Therapies

In addition to the electrical stimulation therapies discussed above with respect to therapies for cardiac remodeling, the physical conditioning of the present subject matter can be integrated into a number of other neural stimulation therapies. Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines, for eating disorders and obesity, and for movement disorders. Many proposed neural stimulation therapies include parasympathetic stimulation through stimulation of the vagus nerve and cardiac branches of the vagus nerve. This listing of other neural stimulation therapies is not intended to be an exhaustive listing.

Figure 3:
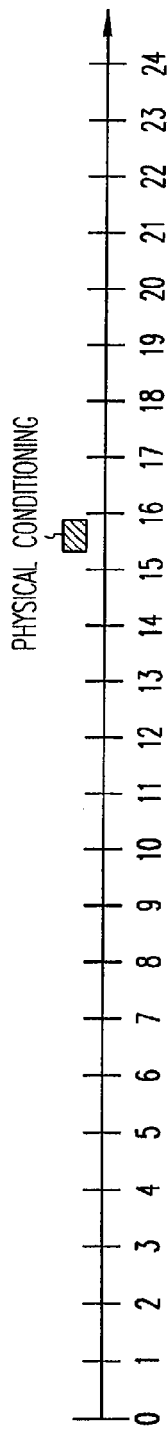
FIG. 3 illustrates a physical conditioning therapy using sympathetic stimulation and/or parasympathetic inhibition, according to various embodiments of the present subject matter.
Figure 4:
FIGS. 4-5 illustrate examples of therapy protocols that combine or integrate sympathetic stimulation and/or parasympathetic inhibition associated with physical conditioning with therapies that use parasympathetic stimulation and/or sympathetic inhibition, according to various embodiments of the present subject matter.
Figure 5:
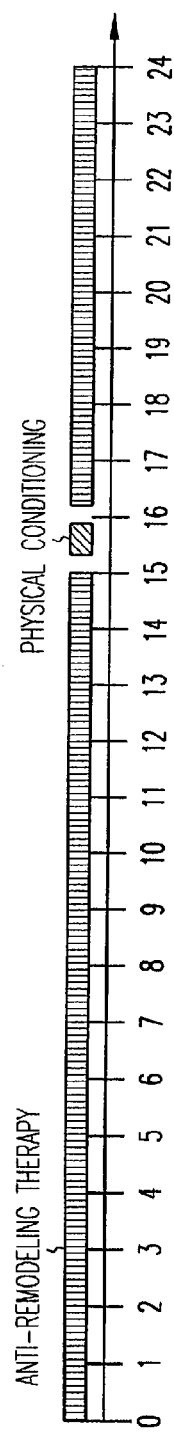

FIG. 3 illustrates a physical conditioning therapy using sympathetic stimulation and/or parasympathetic inhibition, according to various embodiments of the present subject matter, and FIGS. 4-5 illustrate examples of therapy protocols that combine or integrate sympathetic stimulation and/or parasympathetic inhibition associated with physical conditioning with therapies that use parasympathetic stimulation and/or sympathetic inhibition, according to various embodiments of the present subject matter. The time line is divided into 24 intervals, such as may be used to illustrate hours in a day. The illustrated therapies on the time line are intended as an example. Other therapy regimens can be implemented. In FIG. 3, it is illustrated that a physical conditioning therapy is applied for a short duration. This therapy is applied intermittently in some embodiments. Some embodiments apply the physical conditioning in a periodic manner (e.g. daily or every other day). For example, some embodiments apply the stimulation to mimic an exercise regimen (e.g. walk 5 times per week for 30 minutes and maintain a heart rate within a target range). Various embodiments provide the total therapy for the day (e.g. 30 minutes per day) in increments (e.g. 5 minutes of therapy provided 6 times per day) The physical conditioning involves sympathetic stimulation, parasympathetic inhibition, or both sympathetic stimulation and parasympathetic inhibition to intermittently stress the patient. In contrast, an anti-hypertension therapy, for example, applies parasympathetic stimulation, sympathetic inhibition, or both parasympathetic stimulation and sympathetic inhibition. The anti-hypertension therapy can be applied intermittently or periodically (e.g. 5 minutes every hour or 5 seconds every minute). As illustrated generally in FIG. 4, the application of the physical conditioning is timed to occur between anti-hypertension therapy. An anti-remodeling therapy also applies parasympathetic stimulation, sympathetic inhibition, or both parasympathetic stimulation and sympathetic inhibition. The anti-remodeling therapy can be provided on a more continuous basis. As illustrated generally in FIG. 5, the anti-remodeling therapy can be interrupted to provide a window of time in which to provide the physical conditioning therapy. Some embodiments are able to provide parasympathetic stimulation and inhibition at the same site selectable by varying, for example, the frequency of stimulation or polarity of stimulation. Some embodiments are able to provide sympathetic stimulation and inhibition at the same site selectable by varying, for example, the frequency of stimulation or polarity of stimulation. Some embodiments are able to simultaneously provide a local parasympathetic response at a first location and a local sympathetic response in another location.

Hypertension

One neural stimulation therapy involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Examples of afferent nerve trunks that can serve as baroreflex neural targets include the vagus, aortic and carotid nerves. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall. Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Neural Stimulation for Ventricular Remodeling

Another therapy involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity acts synergistically to reverse or prevent cardiac remodeling.

Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves (vagus) inhibits this effect. According to various embodiments, the present subject matter selectively activates the vagal cardiac nerves in addition to CRT in heart failure patients to protect the myocardium from further remodeling and arrhythmogenesis. Other potential benefits of stimulating vagal cardiac nerves in addition to CRT include reducing inflammatory response following myocardial infarction, and reducing the electrical stimulation threshold for defibrillating. For example, when a ventricular tachycardia is sensed, vagal nerve stimulation is applied, and then a defibrillation shock is applied. The vagal nerve stimulation allows the defibrillation shock to be applied at less energy. Also, parasympathetic stimulation may terminate an arrhythmia or otherwise increase the effectiveness of an anti-arrhythmia treatment.

Figure 6B:
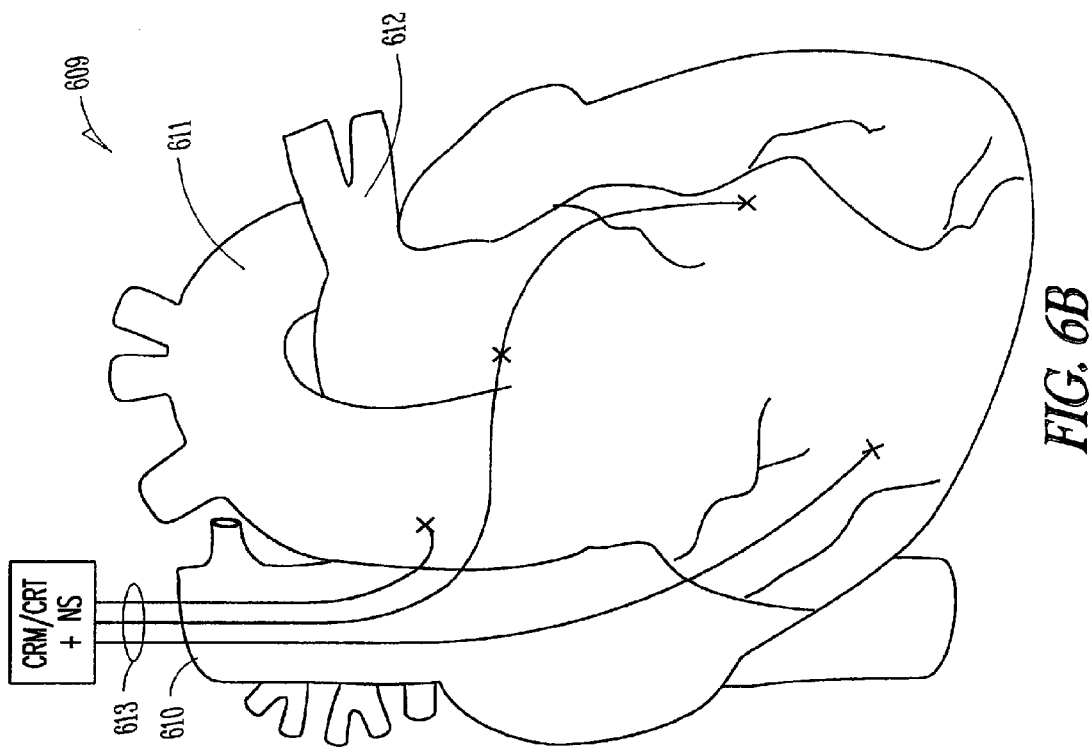
FIGS. 6A-6B illustrate a heart and lead arrangements to provide both myocardial and neural stimulation, according to various embodiments of the present subject matter.
Figure 6A:
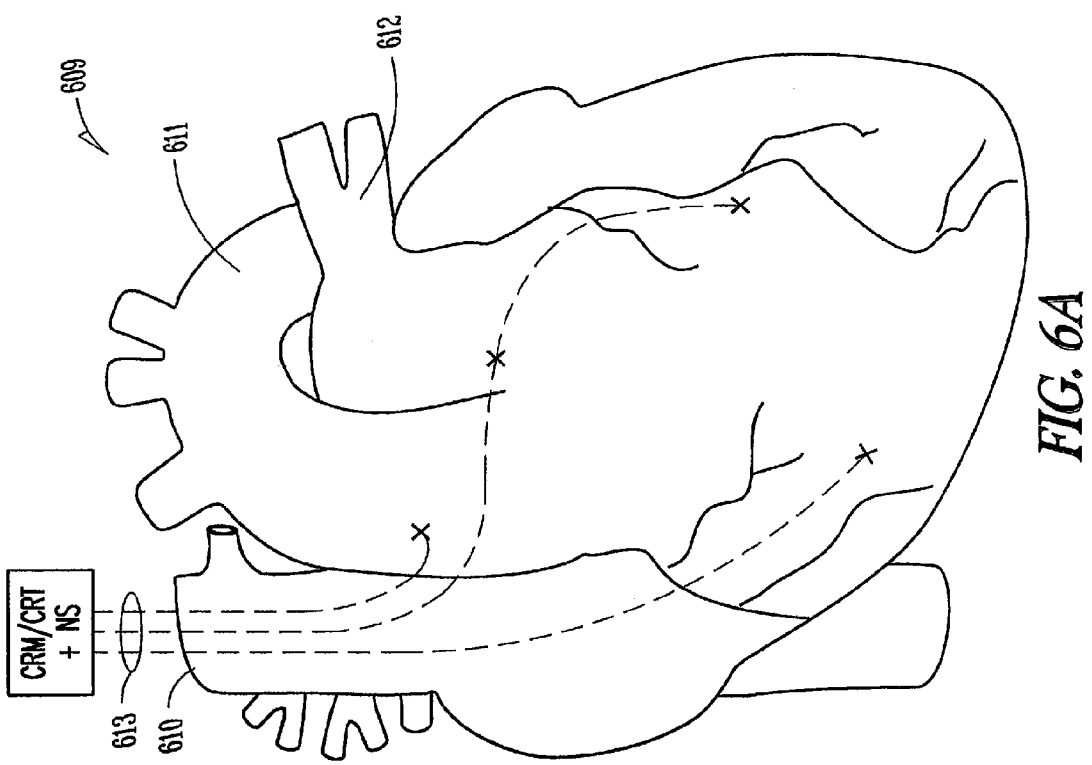

As illustrated in FIGS. 6A and 6B, the heart 609 includes a superior vena cava 610, an aortic arch 611, and a pulmonary artery 612. CRM leads 613 pass nerve sites that can be stimulated in accordance with the present subject matter. FIG. 6A illustrates transvascularly fed leads, and FIG. 6B illustrates epicardial leads. Examples of electrode positions are provided in the drawings by the symbol "X". For example, CRM leads are capable of being intravascularly inserted through a peripheral vein and into the coronary sinus, and are capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. The coronary sinus and pulmonary artery are provided as examples of vasculature proximate to the heart in which a lead can be intravascularly inserted to stimulate nerves within or proximate to the vasculature. Thus, according to various aspects of the present subject matter, nerves are stimulated in or around vasculature located proximate to the heart by at least one electrode intravascularly inserted therein.

Figure 7B:
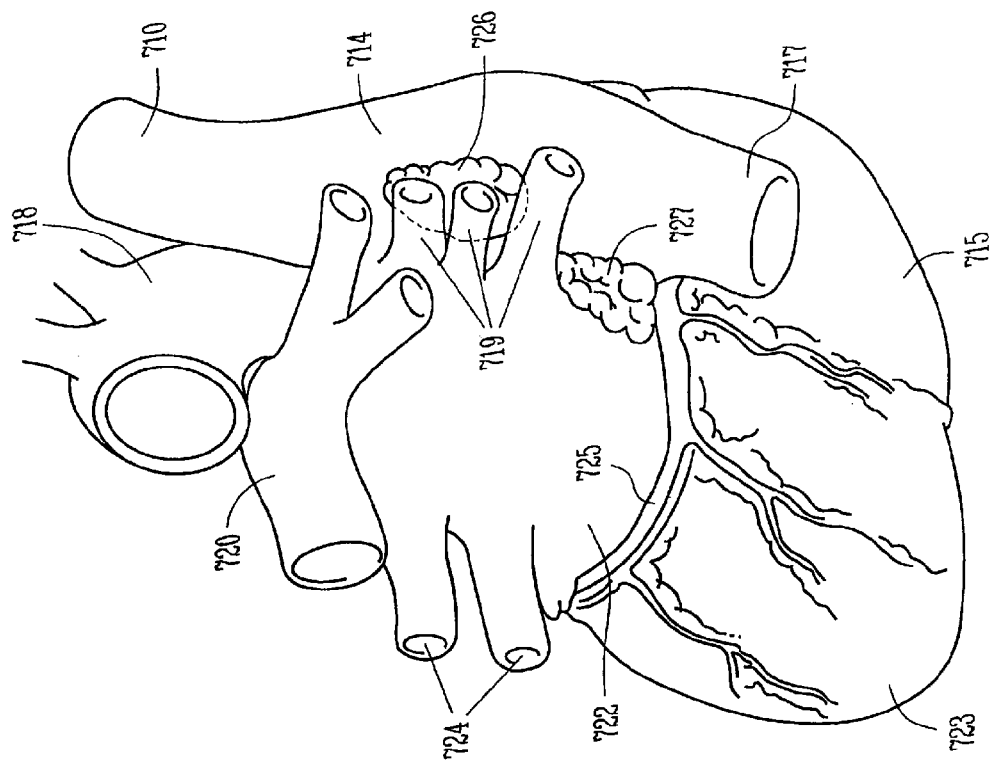
FIGS. 7A-7B illustrate a heart, including cardiac fat pads which are stimulated in various embodiments of the present subject matter.
Figure 7A:
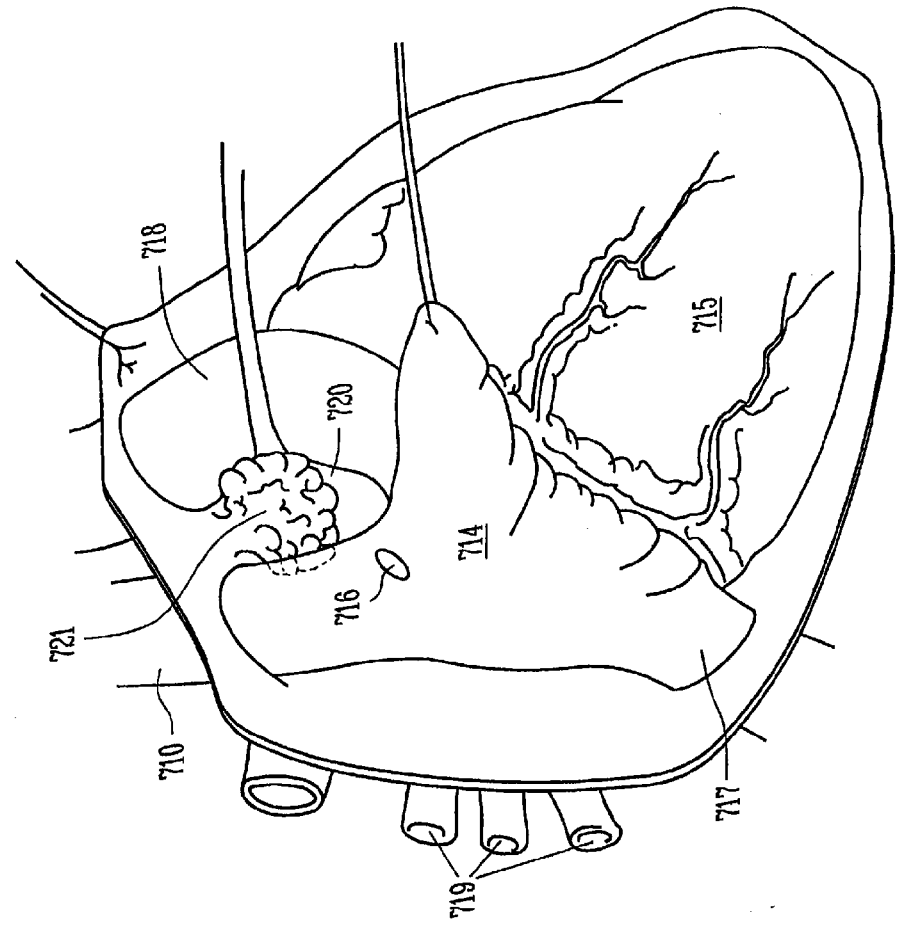

FIGS. 7A and 7B illustrate the right side and left side of the heart, respectively, and further illustrate cardiac fat pads which provide neural targets for some neural stimulation therapies. FIG. 7A illustrates the right atrium 714, right ventricle 715, sinoatrial node 716, superior vena cava 710, inferior vena cava 717, aorta 718, right pulmonary veins 719, and right pulmonary artery 720. FIG. 7A also illustrates a cardiac fat pad 721 between the superior vena cava and aorta. Neural targets in the cardiac fat pad 721 are stimulated in some embodiments using an electrode screwed into or otherwise placed in the fat pad, and are stimulated in some embodiments using an intravenously-fed lead proximately positioned to the fat pad in a vessel such as the right pulmonary artery or superior vena cava, for example. FIG. 7B illustrates the left atrium 722, left ventricle 723, right atrium 714, right ventricle 715, superior vena cava 710, inferior vena cava 717, aorta 718, right pulmonary veins 719, left pulmonary vein 724, right pulmonary artery 720, and coronary sinus 725. FIG. 7B also illustrates a cardiac fat pad 726 located proximate to the right cardiac veins and a cardiac fat pad 727 located proximate to the inferior vena cava and left atrium. Neural targets in the fat pad 726 are stimulated in some embodiments using an electrode screwed into the fat pad 726, and are stimulated in some embodiments using an intravenously-fed lead proximately positioned to the fat pad in a vessel such as the right pulmonary artery 720 or right pulmonary vein 719, for example. Neural targets in the fat pad 727 are stimulated in some embodiments using an electrode screwed into the fat pad, and are stimulated in some embodiments using an intravenously-fed lead proximately positioned to the fat pad in a vessel such as the inferior vena cava 717 or coronary sinus or a lead in the left atrium 722, for example.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used for CRT or in another lead in addition to CRT lead(s).

Intravascularly-fed leads adapted to transvascularly stimulate a target outside of the vessel, also referred to herein as transvascular leads, can be used to stimulate other nerve sites. For example, an embodiment feeds a transvascular stimulation lead into the right azygos vein to stimulate and/or inhibit nerve traffic on the vagus nerve; and an embodiment feeds a transvascular stimulation lead into the internal jugular vein to stimulate and/or inhibit nerve traffic on the vagus nerve. Various embodiments use at least one lead intravascularly fed along a lead path to transvascularly apply neural stimulation and electrically stimulate a cardiac muscle, such as ventricular pacing, as part of CRT.

Other transvascular locations have been mentioned with respect to FIGS. 7A and 7B. Depending on the intravascular location of the neural stimulation electrode(s), the right vagal branch, the left vagal branch or a combination of the right and left vagal branches are capable of being stimulated. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart. Since the venous system is for the most part symmetrical, leads can be fed into an appropriate vessel to transvascularly stimulate the right or left vagus nerve. For example, a lead in the right internal jugular vein can be used to stimulate the right vagus nerve and a lead in the left internal jugular vein can be used to stimulate the left vagus nerve.

The stimulation electrode(s) are not in direct neural contact with the nerve when the transvascular approach to peripheral nerve stimulation is used. Thus, problems associated with neural inflammation and injury commonly associated with direct contact electrodes are reduced.

Device Embodiments

Figure 8:
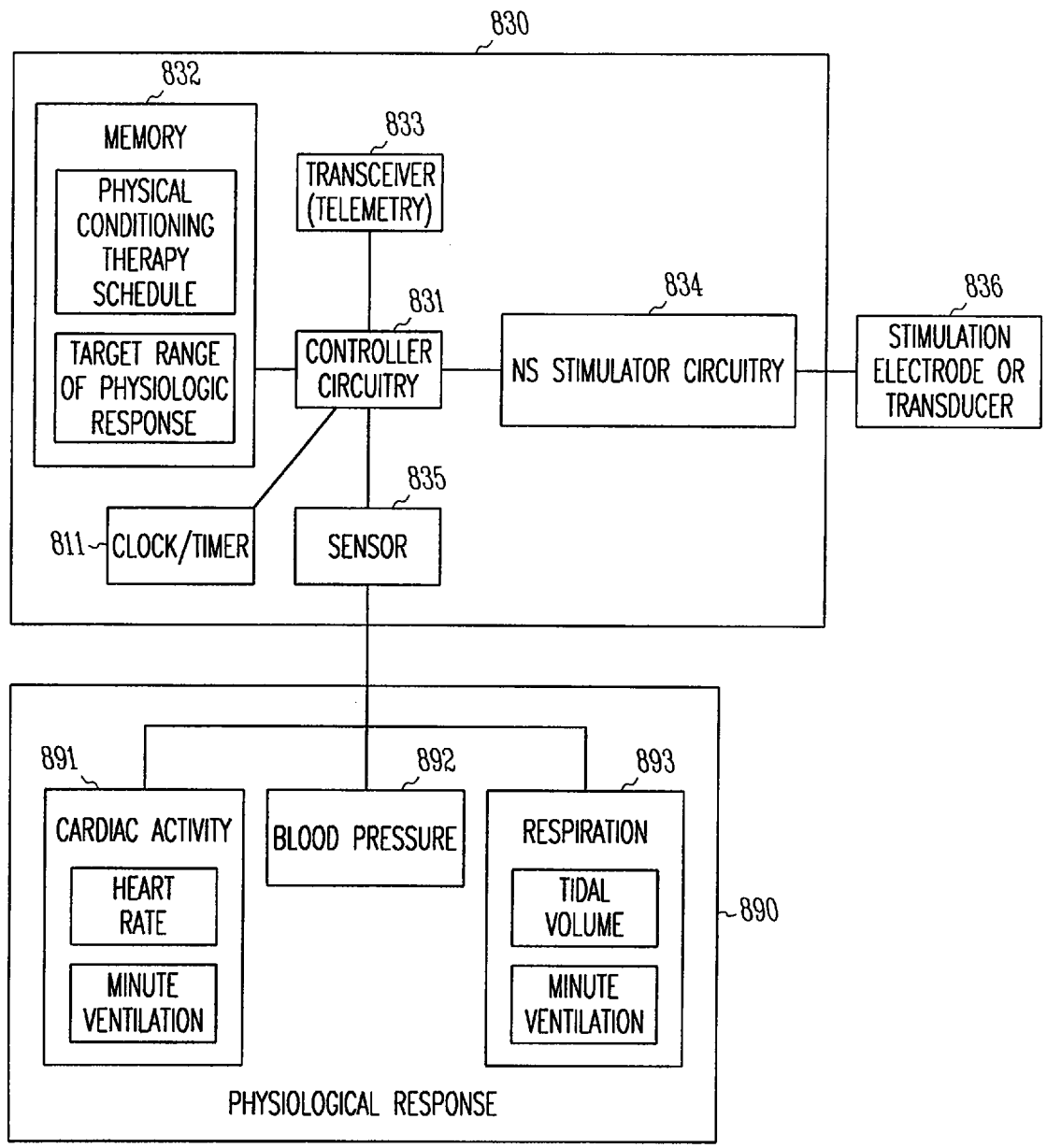
FIG. 8 illustrates an implantable medical device (IMD), according to various embodiments of the present subject matter.

FIG. 8 illustrates an implantable medical device (IMD) 830, according to various embodiments of the present subject matter. The illustrated IMD provides neural stimulation signals for delivery to predetermined neural targets to provide physical conditioning therapy. The illustrated device includes controller circuitry 831 and memory 832. The controller circuitry is capable of being implemented using hardware, software, and combinations of hardware and software. For example, according to various embodiments, the controller circuitry includes a processor to perform instructions embedded in the memory to perform functions associated with the neural stimulation therapy. For example, the illustrated device further includes a transceiver 833 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes neural stimulation circuitry 834. Various embodiments of the device also includes sensor circuitry 835. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes.

According to various embodiments, the neural stimulation circuitry is used to apply electrical stimulation pulses to desired neural targets, such as through one or more stimulation electrodes 836 positioned at predetermined location(s). Some embodiments use transducers to provide other types of energy, such as ultrasound, light or magnetic energy. In various embodiments, the sensor circuitry is used to detect physiological responses. Examples of physiological responses include cardiac activity, such as heart rate and minute ventilation, blood pressure, and respiration, such as tidal volume and minute ventilation. The controller circuitry can compare a target range (or ranges) of the sensed physiological response(s) stored in the memory to the sensed physiological response(s) to appropriately adjust the intensity of the neural stimulation/inhibition.

According to various embodiments, the stimulation circuitry 834 is adapted to set or adjust any one or any combination of stimulation features. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments of the neural stimulation circuitry 834 are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry 834 are adapted to generate a stimulation signal with a predetermined frequency, and are further adapted to respond to a control signal from the controller to modify the frequency of the stimulation signal.

The controller 831 can be programmed to control the neural stimulation delivered by the stimulation circuitry 834 according to stimulation instructions, such as a stimulation schedule, stored in the memory 832. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. For example, if the ON/OFF cycle repeats every 1 minute and the ON time of the duty cycle is 10 seconds, then the duty cycle is 10 seconds per minute. If the ON/OFF cycle repeats every one hour and the ON time is 5 minutes, then the duty cycle is 5 minutes per hour. According to some embodiments, the controller 831 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 831 controls the stimulation circuitry 834 to initiate a neural stimulation session and to terminate the neural stimulation session. The burst duration of the neural stimulation session under the control of the controller 831 can be programmable. The controller may also terminate a neural stimulation session in response to an interrupt signal, such as may be generated by one or more sensed parameters or any other condition where it is determined to be desirable to stop neural stimulation.

The sensor circuitry is used to detect a physiological response 890. The controller 831 compares the response 890 to a target range stored in memory 832, and controls the neural stimulation based on the comparison in an attempt to keep the response 890 within the target range. The target range can be programmable. The physiological response can include cardiac activity 891, blood pressure 892, respiration 893, or various combinations thereof. Examples of cardiac activity sensors include heart rate and minute ventilation sensors. Examples of respiration sensors include tidal volume and minute ventilation sensors.

The illustrated device includes a programmed physical conditioning therapy schedule stored in memory 832 and further includes a clock or timer 811 which can be used to execute the programmable physical conditioning stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the physical conditioning schedule refers to the time intervals or period when the neural stimulation therapy is delivered. A schedule can be defined by a start time and an end time, or a start time and a duration. Various schedules deliver therapy periodically. According to various examples, a device can be programmed with a therapy schedule to deliver therapy from midnight to 2AM every day, or to deliver therapy for one hour every six hours, or to delivery therapy for two hours per day, or according to a more complicated timetable. Various device embodiments apply the therapy according to the programmed schedule contingent on enabling conditions, such as sensed exercise periods, patient rest or sleep, low heart rate levels, and the like. The therapy schedule can also specify how the stimulation is delivered, such as continuously at the pulse frequency throughout the identified therapy period (e.g. 5 Hz pulse frequency for one hour every day), or according to a defined duty cycle during the therapy delivery period (e.g. 10 seconds per minute at 5 Hz pulse frequency for one hour per day). As illustrated by these examples, the therapy schedule is distinguishable from the duty cycle.

Figure 9:
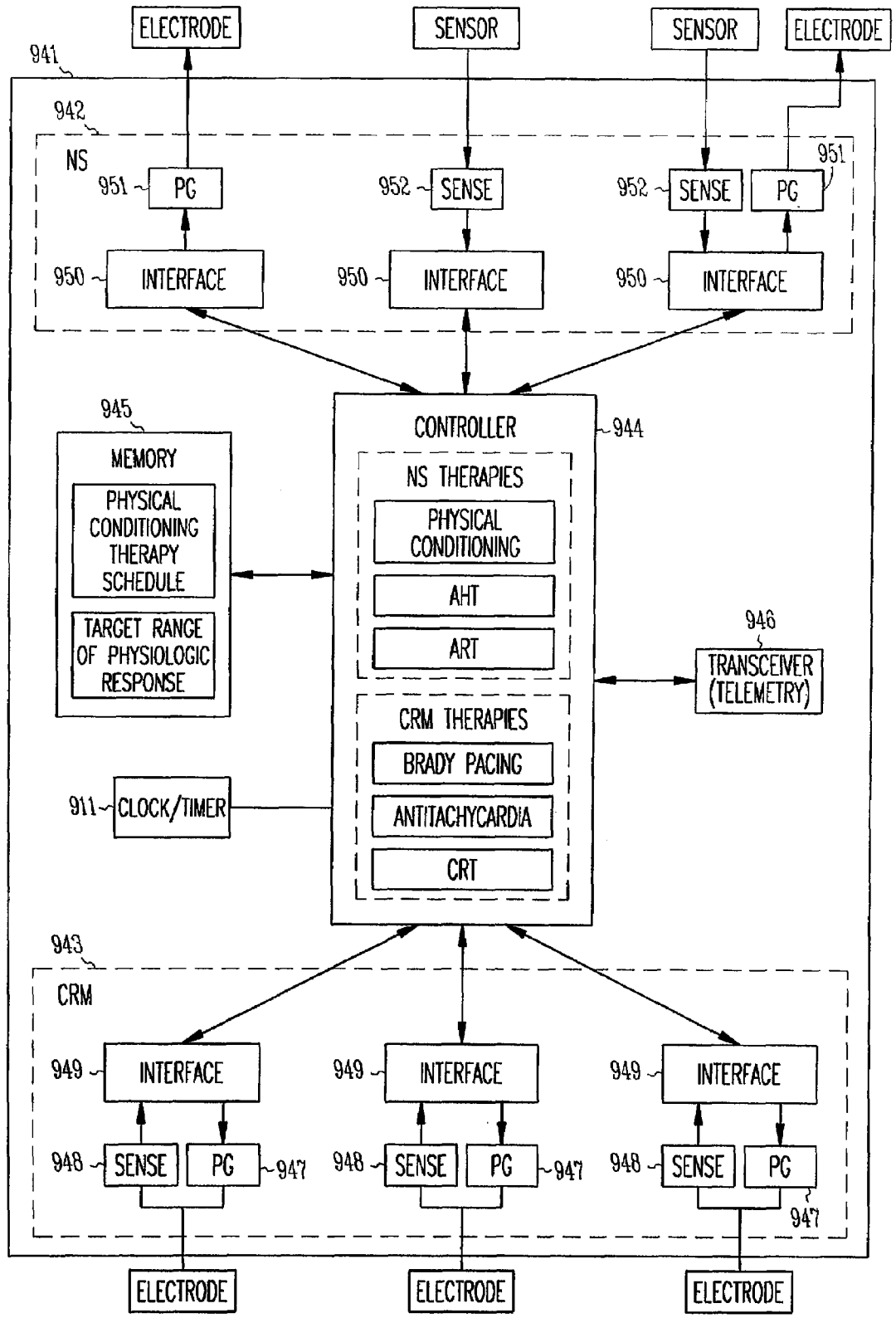
FIG. 9 illustrates an implantable medical device (IMD) having a neural stimulation (NS) component and cardiac rhythm management (CRM) component, according to various embodiments of the present subject matter.

FIG. 9 illustrates an implantable medical device (IMD) 941 having a neural stimulation (NS) component 942 and cardiac rhythm management (CRM) component 943, according to various embodiments of the present subject matter. The illustrated device includes a controller 944 and memory 945. The illustrated memory 945 includes a programmable physical conditioning therapy schedule. The illustrated memory 945 also includes programmable physiological response target(s) that can be used to enable and/or disable the scheduled therapy or to otherwise provide feedback for the therapy.

According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. The neural stimulation therapy includes physical conditioning. Other examples of neural stimulation include anti-hypertension (AHT) therapy and anti-remodeling therapy (ART). Examples of CRM functions include bradycardia pacing, anti-tachycardia therapies such as ATP, defibrillation and cardioversion, and CRT. The controller also executes instructions to detect a tachyarrhythmia. The illustrated device further includes a transceiver 946 and associated circuitry for use to communicate with a programmer or another external or internal device. Various embodiments include a telemetry coil.

The CRM therapy section 943 includes components, under the control of the controller, to stimulate a heart and/or sense cardiac signals using one or more electrodes. The illustrated CRM therapy section includes a pulse generator 947 for use to provide an electrical signal through an electrode to stimulate a heart, and further includes sense circuitry 948 to detect and process sensed cardiac signals. An interface 949 is generally illustrated for use to communicate between the controller 944 and the pulse generator 947 and sense circuitry 948. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 942 includes components, under the control of the controller, to stimulate a neural stimulation target and/or sense parameters associated with nerve activity or surrogates of nerve activity such as blood pressure and respiration. Three interfaces 950 are illustrated for use to provide neural stimulation. However, the present subject matter is not limited to a particular number interfaces, or to any particular stimulating or sensing functions. Pulse generators 951 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 952 are used to detect and process signals from a sensor, such as a sensor of nerve activity, blood pressure, respiration, and the like. The interfaces 950 are generally illustrated for use to communicate between the controller 944 and the pulse generator 951 and sense circuitry 952. Each interface, for example, may be used to control a separate lead. Various embodiments of the NS therapy section only includes a pulse generator to stimulate a neural target.

The illustrated device includes a clock or timer 911, which can be used to execute a programmable physical conditioning stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

Figure 10:
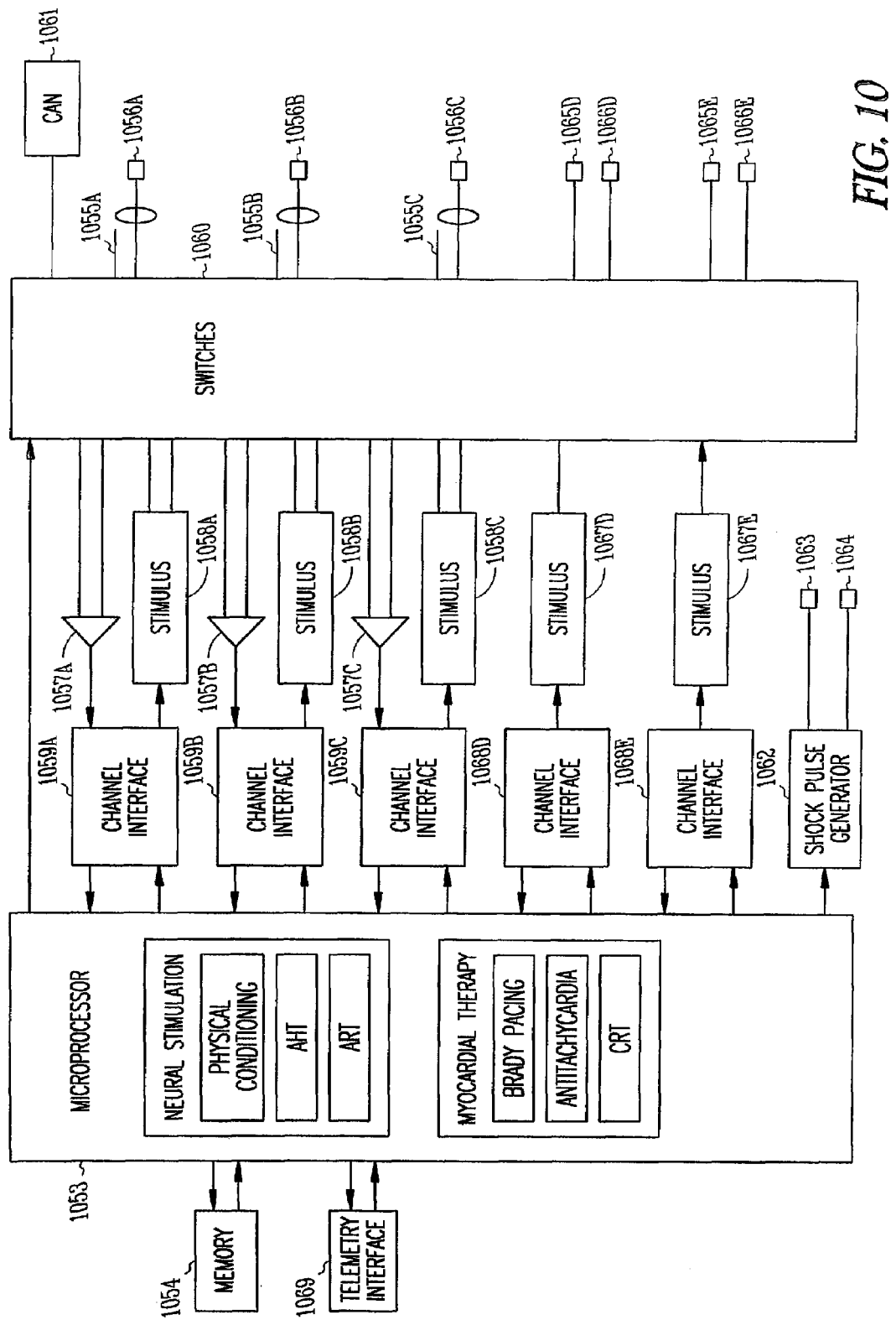
FIG. 10 shows a system diagram of an embodiment of a microprocessor-based implantable device, according to various embodiments.

FIG. 10 shows a system diagram of an embodiment of a microprocessor-based implantable device, according to various embodiments. The controller of the device is a microprocessor 1053 which communicates with a memory 1054 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1055A-C and tip electrodes 1056A-C, sensing amplifiers 1057A-C, pulse generators 1058A-C, and channel interfaces 1059A-C. Each channel thus includes a pacing channel made up of the pulse generator connected to the electrode and a sensing channel made up of the sense amplifier connected to the electrode. The channel interfaces 1059A-C communicate bidirectionally with the microprocessor 1053, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1060 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1061 or an electrode on another lead serving as a ground electrode. A shock pulse generator 1062 is also interfaced to the controller for delivering a defibrillation shock via a pair of shock electrodes 1063 and 1064 to the atria or ventricles upon detection of a shockable tachyarrhythmia.

Neural stimulation channels, identified as channels D and E, are incorporated into the device for delivering parasympathetic inhibition and/or stimulation and/or sympathetic stimulation and/or inhibition, where one channel includes a bipolar lead with a first electrode 1065D and a second electrode 1066D, a pulse generator 1067D, and a channel interface 1068D, and the other channel includes a bipolar lead with a first electrode 1065E and a second electrode 1066E, a pulse generator 1067E, and a channel interface 1068E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1069 connected to the microprocessor, which can be used to communicate with an external device. The illustrated microprocessor 1053 is capable of performing neural stimulation therapy routines and myocardial stimulation routines. Examples of NS therapy routines include physical conditioning therapy (sympathetic stimulation and/or parasympathetic inhibition), anti-hypertension therapy (parasympathetic stimulation and/or sympathetic inhibition), and anti-remodeling therapy (parasympathetic stimulation and/or sympathetic inhibition). Examples of myocardial therapy routines include bradycardia pacing therapies, anti-tachycardia shock therapies such as cardioversion or defibrillation therapies, anti-tachycardia pacing therapies, and cardiac resynchronization therapies.

System Embodiments

Figure 11:
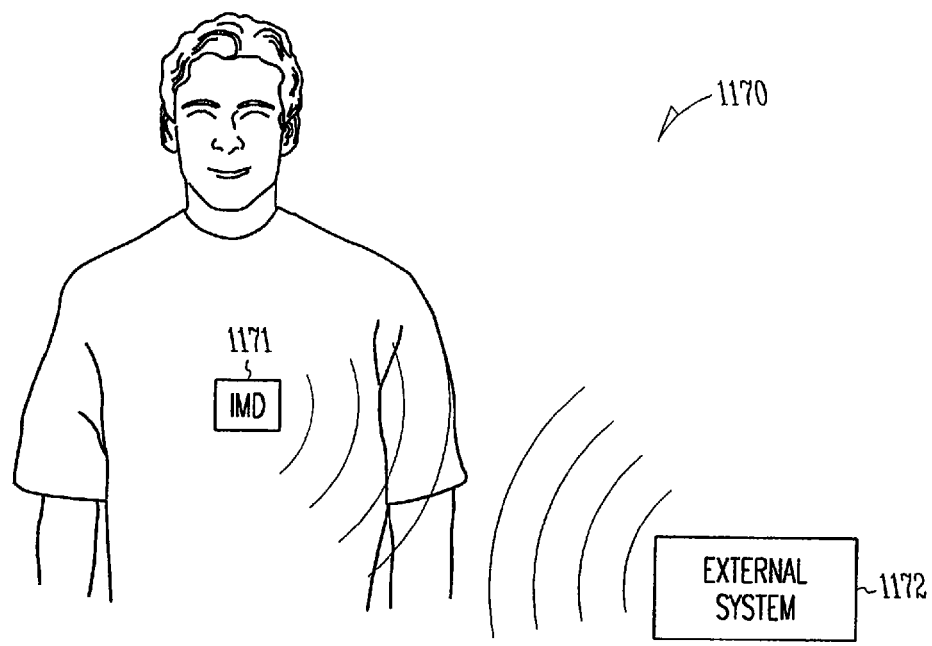
FIG. 11 illustrates a system including an implantable medical device (IMD) and an external system or device, according to various embodiments of the present subject matter.

FIG. 11 illustrates a system 1170 including an implantable medical device (IMD) 1171 and an external system or device 1172, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target to provide a physical conditioning therapy.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 12:
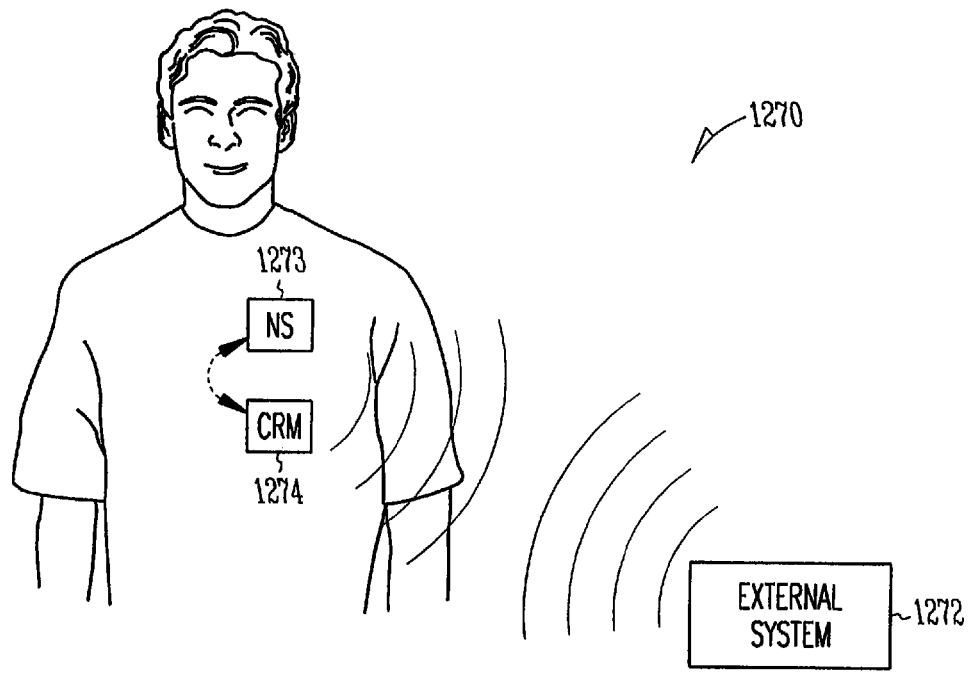
FIG. 12 illustrates a system including an external device, an implantable neural stimulator (NS) device and an implantable cardiac rhythm management (CRM) device, according to various embodiments of the present subject matter.

FIG. 12 illustrates a system 1270 including an external device 1272, an implantable neural stimulator (NS) device 1273 and an implantable cardiac rhythm management (CRM) device 1274, according to various embodiments of the present subject matter. Various aspects involve a method for communicating between an NS device and a CRM device or other cardiac stimulator. In various embodiments, this communication allows one of the devices 1273 or 1274 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Various embodiments target cardiac post-ganglionic neurons, which can be stimulated from a position near the sympathetic ganglia along the spinal cord or from a position over the sympathetic nerve plexus (network) innervating the heart. The sympathetic nerve plexus innervating the heart can be accessed, for example from within a coronary vein overlying a concentration of cardiac sympathetic nerve endings, or in the superior vena cava or pulmonary artery proximate to the cardiac plexus, or in the right atrium septal wall or right ventricle septal wall. According to various embodiments, the design and placement of the neural stimulation electrodes and the stimulation parameters are selected to preferentially stimulate the cardiac neural network and avoid stimulating the myocardium. This preferential neural stimulation may include current field steering designs and methods. Various embodiments synchronize the neural stimulation to the heart rate so that the neural stimulation is triggered to start when the neighboring myocardium is first activated (depolarized) and to last to the end of the refractory period for that myocardium. The end of the refractory period can be a predetermined duration based on typical myocardia refractory times or can be measured by sensing the T-wave of the ECG. The heart rate and T-wave (ECG) can be sensed using a leadless ECG on the can of the implantable medical device, or a lead from the neural stimulator implanted in a chamber of the heart (e.g. right atrium) or a wireless connection to a co-implanted CRM device that is monitoring heart rate and communicating it to the neural stimulator via a wireless link.

Figure 13:
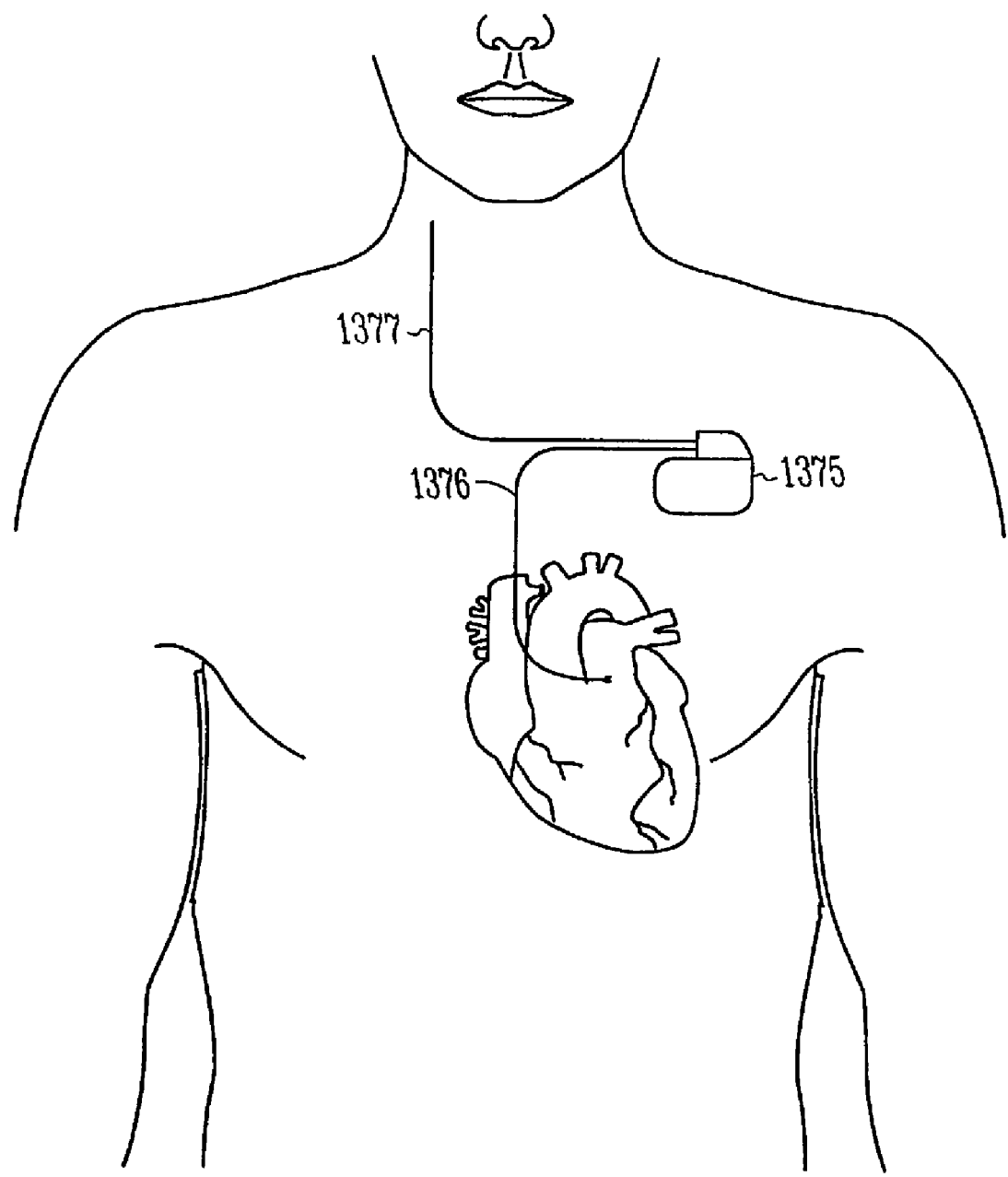
FIG. 13 illustrates an IMD placed subcutaneously or submuscularly in a patient's chest with a lead positioned to provide cardiac post-ganglionic sympathetic nerve plexus stimulation, and with a lead positioned to stimulate and/or inhibit neural traffic in a vagus nerve, by way of example and not by way of limitation, according to various embodiments.

FIG. 13 illustrates an IMD 1375 placed subcutaneously or submuscularly in a patient's chest with a lead 1376 positioned to provide cardiac post-ganglionic sympathetic nerve plexus stimulation, and with a lead 1377 positioned to stimulate and/or inhibit neural traffic in a vagus nerve, by way of example and not by way of limitation, according to various embodiments. Various embodiments include leads to provide a desired CRM therapy. According to various embodiments, neural stimulation lead(s) 1377 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments stimulate/inhibit the vagus nerve using electrode(s) positioned within the internal jugular vein.

Figure 14:
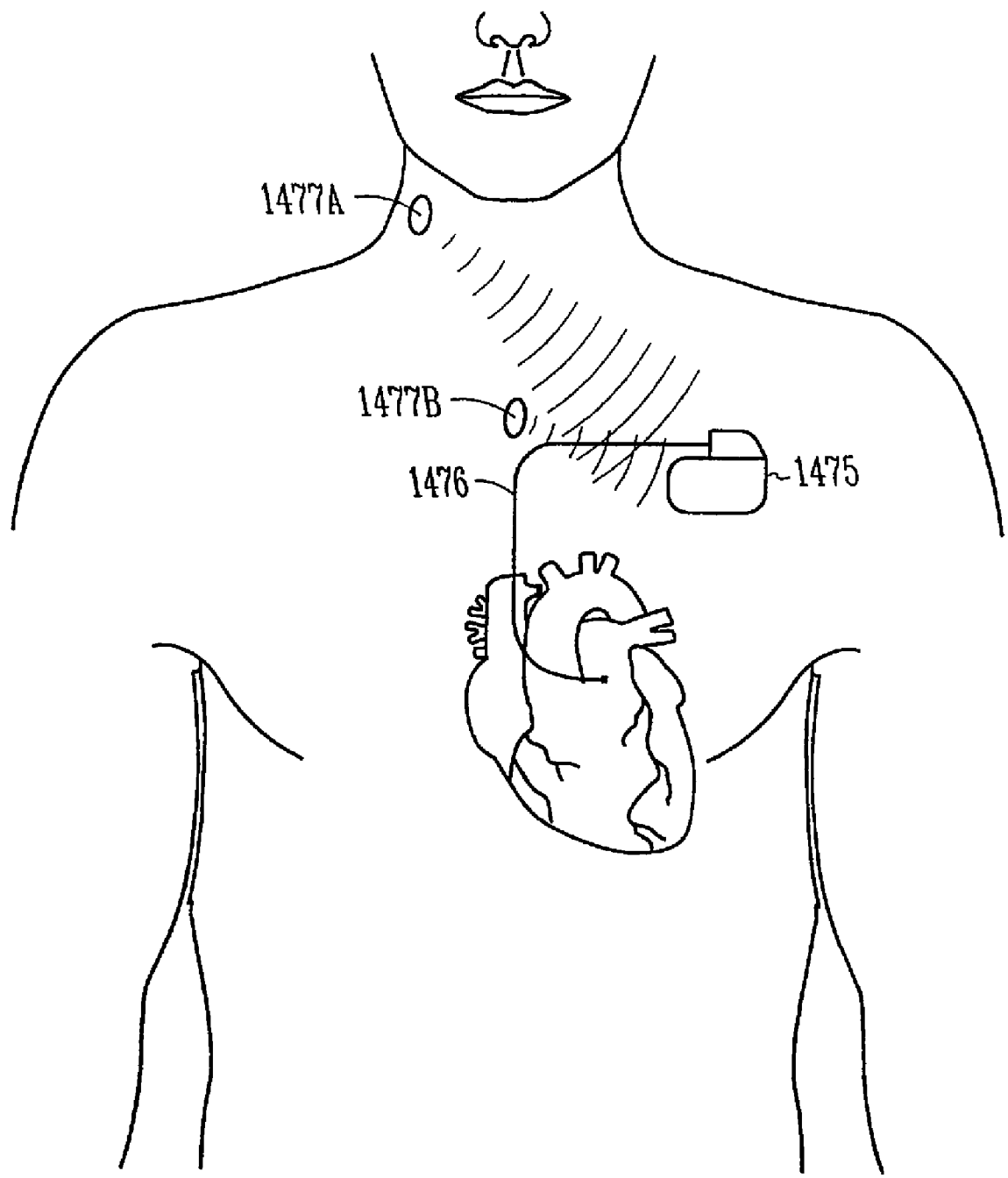
FIG. 14 illustrates an IMD with a lead positioned to provide cardiac post-ganglionic sympathetic nerve plexus stimulation, and with satellite transducers positioned to stimulate/inhibit neural targets, according to various embodiments.

FIG. 14 illustrates an IMD 1475 with a lead 1476 positioned to provide cardiac post-ganglionic sympathetic nerve plexus stimulation, and with satellite transducers 1477A and 1477B positioned to stimulate/inhibit a neural target, according to various embodiments. Transducer 1477A is positioned to stimulate/inhibit the vagus nerve. Transducer 1477B is positioned to stimulate spinal cord sympathetic ganglia. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform cardiac post-ganglionic sympathetic nerve plexus stimulation using wireless links. Examples of satellite transducers include subcutaneous electrodes, nerve cuff electrodes and intravascular electrodes. Some embodiments stimulate/inhibit the vagus nerve using electrode(s) positioned within the internal jugular vein.

Figure 15:
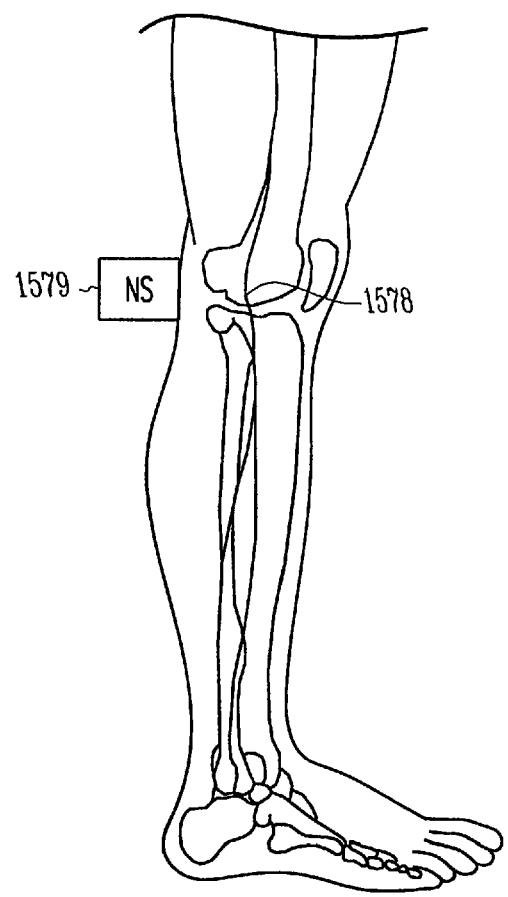
FIG. 15 illustrates a leg, and further illustrates a nerve stimulator adapted to stimulate a peroneal nerve in the leg.

FIG. 15 illustrates a leg, and further illustrates a nerve stimulator 1579 adapted to stimulate a peroneal nerve 1578 in the leg. Various embodiments provide an external neural stimulator, which can be placed behind the knee to stimulate the peroneal nerve and elicit a sympathetic response. Some device embodiments provide an implantable device that can be positioned to stimulate the peroneal nerve. The electrodes or transducers used to stimulate the peroneal nerve can be powered and controlled through a wireless connection or through a tethered connection.

Figure 16:
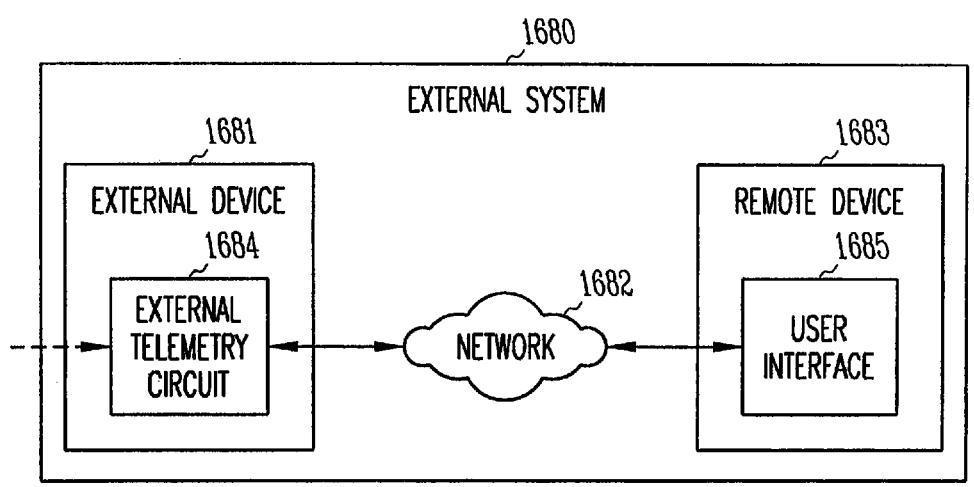
FIG. 16 is a block diagram illustrating an embodiment of an external system.

FIG. 16 is a block diagram illustrating an embodiment of an external system 1680. The external system includes a programmer, in some embodiments. In the illustrated embodiment, the external system includes a patient management system. As illustrated, external system 1680 is a patient management system including an external device 1681, a telecommunication network 1682, and a remote device 1683. External device 1681 is placed within the vicinity of an IMD and includes external telemetry system 1684 to communicate with the IMD. Remote device(s) 1683 is in one or more remote locations and communicates with external device 1681 through network 1682, thus allowing a physician or other caregiver to monitor and treat a patient from a distant location and/or allowing access to various treatment resources from the one or more remote locations. The illustrated remote device 1683 includes a user interface 1685.

One of ordinary skill in the art will understand that the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system, comprising:
   a neural stimulator adapted to generate a stimulation signal adapted to elicit sympathetic activity at a neural target;
   a memory programmed with instructions for delivering a physical conditioning therapy that elicits sympathetic activity correlated to an exercise regimen to mimic a sympathetic response to the exercise regimen; and
   a controller configured to operate on the instructions to control the neural stimulator to intermittently elicit the sympathetic activity correlated to the exercise regimen at the neural target to provide the physical conditioning therapy.

2. The system of claim 1, wherein the instructions programmed in the memory include instructions to, when operated on by the controller, control the neural stimulator to periodically elicit sympathetic activity at the neural target.

3. The system of claim 1, wherein the instructions programmed in the memory include instructions to, when operated on by the controller, control the neural stimulator to intermittently elicit sympathetic activity at the neural target according to a predetermined schedule.

4. The system of claim 1, further comprising a sensor to sense a physiological response indicative of the elicited sympathetic activity.

5. The system of claim 4, wherein the physiological response includes cardiac activity.

6. The system of claim 4, wherein the physiological response includes blood pressure.

7. The system of claim 4, wherein the physiological response includes respiration.

8. The system of claim 1, further comprising a sensor to sense a physiological response, wherein the instructions programmed in the memory include instructions to, when operated on by the controller, adjust stimulation parameters to control the neural stimulator to maintain the physiological response with a target range.

9. The system of claim 8, wherein the physiological response is a heart rate, and the target range is a target heart rate range.

10. The system of claim 1, wherein the instructions programmed in the memory include instructions to, when operated on by the controller, control the neural stimulator to intermittently elicit sympathetic activity by stimulating neural traffic at a sympathetic neural target.

11. The system of claim 10, wherein the sympathetic neural target includes a peroneal nerve.

12. The system of claim 10, wherein the sympathetic neural target includes a sympathetic column in a spinal cord.

13. The system of claim 10, wherein the sympathetic neural target includes cardiac post-ganglionic sympathetic neurons.

14. The system of claim 1, wherein the instructions programmed in the memory include instructions to, when operated on by the controller, control the neural stimulator to intermittently elicit sympathetic activity by inhibiting neural traffic at a parasympathetic neural target.

15. The system of claim 14, wherein the parasympathetic neural target includes a vagus nerve.

16. The system of claim 14, wherein the parasympathetic neural target includes a baroreceptor.

17. The system of claim 14, wherein the parasympathetic neural target includes a cardiac fat pad.

18. The system of claim 1, wherein the instructions programmed in the memory include instructions to, when operated on by the controller, control the neural stimulator to intermittently elicit sympathetic activity for therapy times on the order of two hours or less per day.

19. The system of claim 1, wherein the instructions programmed in the memory include instructions to, when operated on by the controller, further control the neural stimulator to provide a second neural stimulation therapy in addition to the physical conditioning therapy, and the second neural stimulation therapy is adapted to elicit a parasympathetic response.

20. The system of claim 19, wherein the physical conditioning is implemented as part of a heart failure therapy, and the second neural stimulation therapy includes an anti-remodeling therapy (ART).

21. The system of claim 19, wherein the physical conditioning is implemented as part of a heart failure therapy, and the second neural stimulation therapy includes an anti-hypertension therapy (AHT).

22. The system of claim 19, wherein the instructions programmed in the memory include instructions to, when operated on by the controller, control the neural stimulator to avoid simultaneously delivering the physical conditioning therapy and the second neural stimulation therapy.

23. The system of claim 1, further comprising a cardiac rhythm management (CRM) module to provide myocardial stimulation.

24. The system of claim 23, wherein the CRM module, the neural stimulator and the controller are in a single implantable device housing.

25. The system of claim 23, wherein the neural stimulator and the controller are in a first implantable device housing, and the CRM module is in a second implantable device housing, the controller being adapted to communicate to the CRM module.

26. The system of claim 1, wherein the controller and the neural stimulator are in an external device housing.

27. The system of claim 1, wherein the instructions programmed in the memory include instructions to, when operated on by the controller, respond to a signal triggered by a user to initiate a session of the physical conditioning therapy.

28. The system of claim 1, wherein the instructions programmed in the memory include instructions to, when operated on by the controller, respond to a signal triggered by a user to terminate a session of the physical conditioning therapy.

29. The system of claim 1, wherein the instructions programmed in the memory include instructions to, when operated on by the controller, respond to a signal triggered by a user to titrate the physical conditioning therapy.

30. The system of claim 1, wherein the instructions programmed in the memory include instructions to, when operated on by the controller,
respond to a first signal triggered by a user to initiate a therapy session;
respond to a second signal triggered by the user to terminate the therapy session; and
respond to a third signal triggered by the user to titrate the therapy.

31. A method, comprising: providing a physical conditioning therapy, wherein providing the physical conditioning therapy includes eliciting sympathetic activity correlated to an exercise regimen to mimic a sympathetic response to the exercise regimen, wherein eliciting sympathetic activity includes intermittently stimulating a neural target to elicit the sympathetic activity correlated to the exercise regimen.

32. The method of claim 31, further comprising manually initiating the stimulation of the neural target and manually terminating the stimulation of the neural target for each episode of the intermittent stimulation.

33. The method of claim 31, further comprising automatically initiating the stimulation of the neural target and automatically terminating the stimulation of the neural target for each episode of the intermittent stimulation.

34. The method of claim 31, further comprising adjusting neural stimulation parameters to achieve a target physiological response to the physical conditioning therapy.

35. The method of claim 34, wherein the target physiological response includes a target heart rate.

36. The method of claim 34, wherein the target physiological response includes a target blood pressure.

37. The method of claim 34, wherein the target physiological response includes a target respiration.

38. The method of claim 31, further comprising integrating a neural stimulation therapy to elicit a parasympathetic response with the physical conditioning therapy.

* * * * *

UNITED STATES PATENT AND TRADEMARK OFFICE
CERTIFICATE OF CORRECTION

| | | |
|---|---|---|
| PATENT NO. | : 7,647,101 B2 | Page 1 of 1 |
| APPLICATION NO. | : 11/423249 | |
| DATED | : January 12, 2010 | |
| INVENTOR(S) | : Libbus et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this

Twenty-eighth Day of December, 2010

David J. Kappos
*Director of the United States Patent and Trademark Office*